United States Patent
Vartiovaara et al.

(10) Patent No.: US 10,261,114 B1
(45) Date of Patent: Apr. 16, 2019

(54) DEVICE AND METHOD FOR DEVICE DETECTION USING ELECTRICAL NON-LINEAR CHARACTERISTICS

(71) Applicant: GENERAL ELECTRIC COMPANY, Schenectady, NY (US)

(72) Inventors: Ville Petteri Vartiovaara, Tuusula (FI); Ari Pitkanen, Vantaa (FI)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 0 days.

(21) Appl. No.: 15/831,540

(22) Filed: Dec. 5, 2017

(51) Int. Cl.
 *G01R 19/165* (2006.01)
 *H04L 29/08* (2006.01)
 *H04W 84/02* (2009.01)
 *H04L 5/00* (2006.01)

(52) U.S. Cl.
 CPC ........ *G01R 19/16566* (2013.01); *H04L 67/12* (2013.01); *H04W 84/02* (2013.01); *H04L 5/0048* (2013.01); *H04L 67/1097* (2013.01)

(58) Field of Classification Search
 CPC .......... G01R 19/16566; H04L 67/12

USPC .......... 340/13.2–13.25
See application file for complete search history.

(56) References Cited

U.S. PATENT DOCUMENTS

| | | | |
|---|---|---|---|
| 2013/0063027 A1* | 3/2013 | Recker | H05B 33/0803 315/86 |
| 2016/0135741 A1* | 5/2016 | Chetham | A61B 5/6833 600/391 |
| 2017/0325684 A1* | 11/2017 | Vartiovaara | A61B 5/0017 |

* cited by examiner

*Primary Examiner* — Allen T Cao (57) ABSTRACT

Devices and methods for detecting a medical sensor device being attached to a host device are disclosed. The host device includes a reader circuit that can generate an AC pilot signal. When the medical sensor device is being attached to the host device, the AC pilot signal is fed to a non-linear circuit in the sensor device, which responds with a DC signal. The host device compares the magnitude of the response signal with a threshold magnitude. If the magnitude of the response signal is greater than the threshold magnitude, the host device determines that the sensor device is being attached and establishes connection with the sensor device.

18 Claims, 7 Drawing Sheets

FIG. 7

DEVICE AND METHOD FOR DEVICE DETECTION USING ELECTRICAL NON-LINEAR CHARACTERISTICS

TECHNICAL FIELD

This disclosure relates to devices and methods for detecting the attachment of a medical sensor device to a host device.

BACKGROUND

Medical sensor devices are widely used in care delivery areas such as patient monitoring and fetal monitoring for monitoring physiological conditions of patients or fetuses, such as Electrocardiography (ECG), electroencephalograph (EEG), blood pressure, temperature, heart rate, oxygen saturation, etc. Oftentimes, a medical sensor device is connected to a host device, which can supply power to the sensor device for operation and receive physiological data acquired by the sensor device. The host device can process the physiological data, display the physiological condition for review, and/or transmit the physiological data to a remote processing/storage system. When the sensor device is being attached to the host device, the host device needs to detect the presence of the sensor device and react by, for example, initiating a handshake sequence with the sensor device and/or turning on the power to the sensor device, thereby establishing the power/communication connection with the sensor device. Mechanically switches, optical detectors, magnetic detectors have been used to detect the attachment of the sensor device. However, mechanical switches are prone to wear out or stalling. Optical detectors and magnetic detectors add complexity and cost to the patient monitoring system. A reliable and cost-efficient method for detecting the presence of the sensor device is generally desired.

SUMMARY

In one embodiment, the present disclosure provides a host device for medical sensor devices. The host device comprises a connector comprising a first connection point and a second connection point configured to connect to a medical sensor device. The host device also comprises a reader circuit configured to generate an AC pilot signal supplied at the first connection point and the second connection point. The host device further comprises a processor configured to receive a response signal from the first connection point and the second connection point, compare a magnitude of the response signal with a threshold magnitude, and in response to determining the magnitude of the response signal is greater than the threshold magnitude, establish a connection with the medical sensor device being attached to the host device.

In another embodiment, the present disclosure provides a medical sensor device comprising a sensor for monitoring physiological conditions of a patient or a fetus. The medical sensor device also comprises a connector comprising a first connection point and a second connection point configured to connect to a host device. The medical sensor device further comprises a non-linear circuit disposed between the first connection point and a second connection point. The non-linear circuit is configured to generate a direct current (DC) response signal in response to an AC pilot signal received from the host device via the connector.

In yet another embodiment, the present disclosure provides a method for detecting a medical sensor device being attached to a host device. The host device comprises a first connection point and a second connection point configured to connect to the medical sensor device. The method comprises generating an AC pilot signal supplied at the first connection point and the second connection point, receiving a response signal from the first connection point and the second connection point, and comparing a magnitude of the response signal with a threshold magnitude. The method further comprises in response to determining the magnitude of the response signal is greater than the threshold magnitude, establishing a connection with the medical sensor device being attached to the host device.

BRIEF DESCRIPTION OF THE DRAWINGS

Various aspects of this disclosure may be better understood upon reading the following detailed description and upon reference to the drawings in which.

The drawings illustrate specific aspects of the described components, systems and methods for detecting attachment of a medical sensor device to a host device. Together with the following description, the drawings demonstrate and explain the principles of the structures, methods, and principles described herein. In the drawings, the size of components may be exaggerated or otherwise modified for clarity. Well-known structures, materials, or operations are not shown or described in detail to avoid obscuring aspects of the described components, systems and methods.

DETAILED DESCRIPTION

One or more specific embodiments of the present disclosure are described below in order to provide a thorough understanding. These described embodiments are only examples of the devices and systems for detecting the attachment of a medical sensor device to a host device. The skilled artisan will understand that specific details described in the embodiments can be modified when being placed into practice without deviating the spirit of the present disclosure.

When introducing elements of various embodiments of the present disclosure, the articles "a," "an," and "the" are intended to mean that there are one or more of the elements. The terms "first," "second," and the like, do not denote any order, quantity, or importance, but rather are used to distinguish one element from another. The terms "comprising," "including," and "having" are intended to be inclusive and mean that there may be additional elements other than the listed elements. As the terms "connected to," "coupled to," etc. are used herein, one object (e.g., a material, element, structure, member, etc.) can be connected to or coupled to another object regardless of whether the one object is directly connected or coupled to the other object or whether there are one or more intervening objects between the one object and the other object. In addition, it should be understood that references to "one embodiment" or "an embodiment" of the present disclosure are not intended to be interpreted as excluding the existence of additional embodiments that also incorporate the recited features.

Referring to the figures generally, the present disclosure is to provide devices and methods for detecting a medical sensor device being attached to a host device. The medical sensor device can be, for example, ECG monitor, EEG monitor, non-invasive blood pressure (NIBP) monitor, pulse oximeter, temperature monitor, or any suitable device for monitoring physiological conditions of a patient or a fetus. The host device can supply power to the medical sensor device for operation and receive physiological data acquired by the sensor device. The sensor device can be connected to the host device through an interface, which includes a connector at the sensor device side and a connector at the host device side. The host device includes a reader circuit that can generate an alternating current (AC) excitation signal. When the sensor device is being attached to the host device, the AC excitation signal is fed, through the interface, to a non-linear circuit in the sensor device, which responds with a direct current (DC) signal. Due to the non-linear characteristics of the circuit, the magnitude of the response signal generated by the non-linear circuit is greater than what a linear element would generate. The host device compares the magnitude of the response signal with a predefined threshold magnitude. If the magnitude of the response signal is greater than the threshold magnitude, the host device determines that the sensor device is present and establishes a connection with the sensor device.

The detection method is safe to a patient because the AC excitation signal provided by the reader circuit has a low AC power (e.g., 0.5 VAC), which does not cause excessive leakage current. Wrong detection risk is low because human skin or saline solution, which are essentially linear elements, cannot generate as high DC level as the non-linear circuit does. In addition, the detection method is low-cost and reliable because no moving parts are used.

Figure 1:
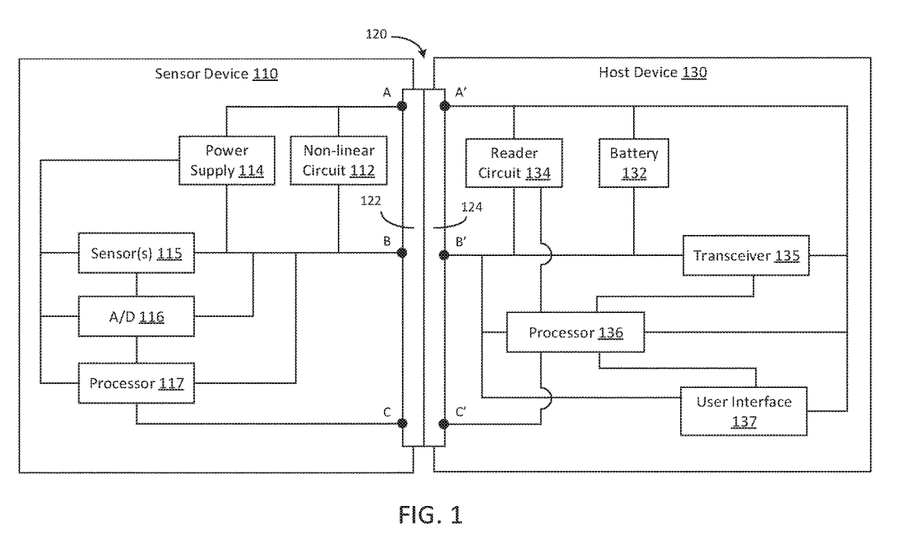
FIG. 1 is a block diagram of a medical sensor device and a host device connected with each other, in accordance with an exemplary embodiment.

Now referring to FIG. 1, a block diagram of a medical sensor device 110 and a host device 130 connected with each other is shown, in accordance with an exemplary embodiment. As illustrated in FIG. 1, in some embodiments, the sensor device 110 and the host device 130 are connected through an interface 120, which includes a first connector 122 at the sensor device side and a second connector 124 at the host device side. In some embodiments, the interface 120 can transfer power from the host device 130 to the sensor device 110. In some embodiments, the interface 120 can communicate data between the sensor device 110 and the host device 130.

As illustrated in FIG. 1, in some embodiments, the medical sensor device 110 includes a connector 122, non-linear circuit 112, power supply 114, one or more sensor(s) 115, analog-to-digital (A/D) converter 116, and processor 117. The sensor device 110 may include any sensor(s) 115 for sensing patient/fetal physiological conditions. For example, the sensor device 110 may be an ECG monitor wherein the sensor(s) 115 include ECG electrodes. The sensor device 110 may be an EEG monitor wherein the sensor(s) 115 include EEG electrodes. The sensor device 110 may be a NIBP monitor wherein the sensor(s) 115 include a blood pressure sensor. The sensor device 110 may be a peripheral oxygen saturation (SpO2) monitor wherein the sensor(s) 115 include a pulse oximeter. The sensor device 110 may be a temperature monitor wherein the sensor(s) 115 include a thermometer.

In some embodiments, the sensor device 110 may be attached to a patient by various mechanism so that the device can be worn or maintained on or near the patient. For example, an ECG monitor may be attached to a patient via a chest strap or a waist strap. An EEG monitor may be attached to a patient by a headband, neckband, chest band, or armband, or may be attached directly to an ECG electrode or a separate accessory adhered to the skin of the patient. A NIBP monitor may be attached to a cuff which may be worn by the patient. A pulse oximeter may be attached to a wristband which may be worn by the patient. In some embodiments, the sensor device 110 may be disposable for hygienic purposes.

The A/D converter 116 can digitize the physiological signals acquired by the sensor(s) 115. The A/D converter 116 may be any device or logical set capable of digitizing analog signals. In some embodiments, the A/D converter 116 includes an Analog Front End (AFE).

In some embodiments, the sensor device 110 includes a processor 117 which receives the digital physiological data from the A/D converter 116 and transmits the data to the host device 130 via the interface 120. In addition, the processor 117 may be configured to perform various functions, depending on the type of sensor(s) 115. For example, if the sensor(s) 115 include ECG electrodes, the processor 117 may be configured to determine a heart rate. If the sensor(s) 115 include EEG electrodes, the processor 117 may be configured to determine a depth of anesthesia measurement value, such as an entropy value or a sedation responsiveness index value. If the sensor(s) 115 includes a blood pressure sensor, the processor 117 may be configured to calculate systolic, diastolic and/or mean blood pressure values. If the sensor(s) 115 include a pulse oximeter, the processor 117 may be configured to determined blood oxygenation value.

In some embodiments, the sensor device 110 does not include a processor. For example, if the sensor(s) 115 include a thermometer for sensing a patient's temperature, the sensor device 110 may be a relatively simple device without a processor. In addition, the temperature sensor device may be disposable, thus it would be cost efficient not to include a processor. In this case, the A/D converter 116 sends the digital physiological data to the host device 130 via the interface 120.

The power supply 114 supplies power to the sensor(s) 115, A/D converter 116, and processor 117. In some embodiments, the power supply 114 includes conductors that conduct power received from the host device 130 via the interface 120. In some embodiments, the power supply 114 includes a battery that is charged by the host device 130 via the interface 120 and distributes power to the various components of the sensor device 110. In further embodiments where the sensor device 110 involves demanding electromechanical functions (e.g., NIBP sensing), the power supply 114 has power management capabilities.

The non-linear circuit 112 can generate a DC signal in response to an AC excitation signal received from the host device 130 via the interface 120. When the host device 130 detects the DC signal via the interface 120, the host device 130 determines that the sensor device 110 is attached to it. The non-linear circuit 112 comprises a non-linear element (e.g., diode, transistor) so that the circuit can generate a DC level higher than what linear elements, such as human skin and saline solution, generate in response to the AC excitation signal. Structure of the non-linear circuit 112 will be discussed in detail below with reference to FIGS. 3A and 3B.

It should be understood that the medical sensor device 110 as shown in FIG. 1 is for illustration not for limitation. Any suitable sensor device may be used, which may have more, fewer, and/or different components than what are shown in FIG. 1.

In some embodiments, the host device 130 is a device that relays information between the sensor device 110 and a remote processing system, such as a central monitoring station and/or a central storage location (not shown in the present Figure), via a wireless connection, such as antenna or access point. The central monitoring station provides a central location for clinicians to monitor patient status and/or receive alarm notifications. In some embodiments, the central monitoring station includes a local network with servers housed within a medical facility. In some embodiments, the central monitoring station includes a cloud-based system hosted by a cloud computing provider. The central storage location can store patient information which may be part of a patient's medical record and may be accessible by clinicians.

In some embodiments, the host device 130 is a device that relays information between the sensor device 110 and a transceiver proximate to the patient (not shown in the present Figure) via a wireless connection. The proximate transceiver communicates with a remote processing system (e.g., central monitoring station, central storage location) via a wireless connection. For example, the host device 130 can be a generic activator module as disclosed in patent application Ser. No. 15/153,979, which is incorporated herein by reference. The generic activator module can be connected to various types of sensor devices.

As illustrated in FIG. 1, in some embodiments, the host device 130 includes a battery 132, reader circuit 134, transceiver/transmitter 135, processor 136, and user interface 137. The processor 136 receives the digital physiological data transmitted from the sensor device 110 via the interface 120. In some embodiments, the processor 136 is further configured to process the digital physiological data. For example, the processor 136 may be configured to determine the type of the sensor device 110 to which the host device 130 is connected and process the data based on the type of the sensor device 110.

The processor 136 operates a transceiver or transmitter 135 to transmit data to a remote or proximate processing system, where the data may be further processed, stored, and/or transmitted. For the simplicity of expression, transceiver is used herein to include both transceiver and transmitter. The transceiver 135 may include any device for wirelessly transmitting data. In some embodiments, the transceiver 135 uses protocols for body area network (BAN), such as medical body area network (MBAN), used by wearable or portable computing devices. In some embodiments, the transceiver 135 uses protocols for wireless medical telemetry service (WMTS) or a Wi-Fi compliant wireless local area network (WLAN). In some embodiments, the transceiver 135 uses protocols for Bluetooth, Bluetooth Low Energy (BLE), ANT, and ZigBee, etc.

The processor 136 operates a user interface 137 to display physiological information about a patient (or a fetus) so that a clinician can view details/aspects of the patient's physiological condition from the user interface 137. The displayed physiological information may be calculated by the processor 136 based on the digital physiological data received from the sensor device 110. For example, if the sensor device 110 is an ECG monitor, the processor 136 may process the ECG data received from the sensor device 110 to calculate a heart rate, and display the heart rate on the user interface 137. In some embodiments where the sensor device 110 transmits a heart rate to the host device 130, the processor 136 may simply operate to display the heart rate on the user interface 137.

Besides physiological information, the user interface 137 may display various types of information such as but not limited to, the charge level of the battery 132, the sensor device 110 connected to the host device 130, malfunction of the sensor device 110 or the host device 130, and so on.

The reader circuit 134 can generate a low-power AC excitation signal to feed to the sensor device 110 via the interface 120. When the non-linear circuit 112 responds with a DC signal, the reader circuit 134 can receive the DC signal via the interface 120. Structure of the reader circuit 134 will be discussed in detail below with reference to FIG. 2.

The battery 132 supplies power to the reader circuit 134, transceiver 135, processor 136, and user interface 137. Furthermore, when the sensor device 110 is connected to the host device 130, power is further distributed from the battery 132 to the sensor device 110 via the interface 120. The battery 132 may be any battery capable of providing sufficient power and in some embodiments, includes a rechargeable battery. In some embodiments, the host device 130 includes a voltage regulator (not shown in the present Figure) connected to the battery 132 and configured to regulate the power distribution within the host device 130 and to the sensor device 110.

It should be understood that the host device 130 as shown in FIG. 1 is for illustration not for limitation. Any suitable host device 130 may be used, which may have more, fewer, and/or different components than what are shown in FIG. 1.

The interface 120 is comprised of a first connector 122 at the side of the sensor device 110 and a second connector 124 at the side of the host device 130. The interface 120 can transfer power from the host device 130 to the sensor device 110 and data (e.g., physiological data) between the sensor device 110 and the host device 130. In some embodiments, the host device side connector 124 is configured to connect with the connector 122 of various types of sensor devices. For example, the connector 122 may be configured identically for various types of sensor devices. Alternatively, the connector 122 may be configured differently for various types of sensor devices. For example, the connector 122 may have more or fewer connection points for transferring digital physiological data and power depending on the type of sensor device 110 and how many data channels are collected. Although one connector 122 is shown on the sensor device side and one connector 124 is shown on the host device side, it should be understood that multiple connectors can be used at one or both sides. For example, separate connectors can be used for power transfer and data transfer.

As shown in FIG. 1, in some embodiments, the interface 120 includes three pair of connection points A and A', B and B', and C and C', where A-A' and B-B' are used for transferring power (e.g., A-A' are power terminals and B-B' are ground terminals) and C-C' for transferring data. It should be understood that connections points A-A', B-B', and C-C' are for illustration not for limitation, the interface 120 may include any suitable number of connection points.

In some embodiments, A-A' and B-B' are electrical contacts. For example, connections points A and B may include one or more pins and connection points A' and B' may include one or more ports corresponding to the pins (e.g., universal connection ports). For example, A and B can be implemented as a pin which includes a tip surrounded by a ring. A' and B' can be implemented as a mating pad, which comprises a recessed receptacle configured to receive the tip and a ring surrounding the recessed receptacle configured to be in contact with the ring of pin. In some embodiments, A-A' and B-B' include aligned inductive coils connected through inductive coupling, or capacitors connected through capacitive coupling, or any connection mechanism capable of transferring power between the sensor device 110 and the host device 130.

Connection points C-C' may include any suitable mechanism capable of transferring data between the sensor device 110 and the host device 130. In some embodiments, C-C' include electrical contacts configured as I²C or serial peripheral interface (SPI). In some embodiments, C-C' are implemented using short range wireless communication such as Bluetooth, near field communication (NFC), ANT, etc. In some embodiments, connection point C includes an optical data port formed on the sensor device 110 and connection point C' includes an optical data port formed on the host device 130. C-C' can be physically aligned with each other such that an optical data path can be formed to transmit data between the sensor device 110 and the host device 130 through the mating optical data ports.

In some embodiments, the connector 122 (or 124) may be inserted into or otherwise connected with the connector 124 (or 122) so that the sensor device 110 is attached to the host device 130. In some embodiments, the connection between the sensor device 110 and the host device 130 does not require physical contact, for example, when the devices are connected via an optical data transfer and a capacitive power transfer.

Figure 2:
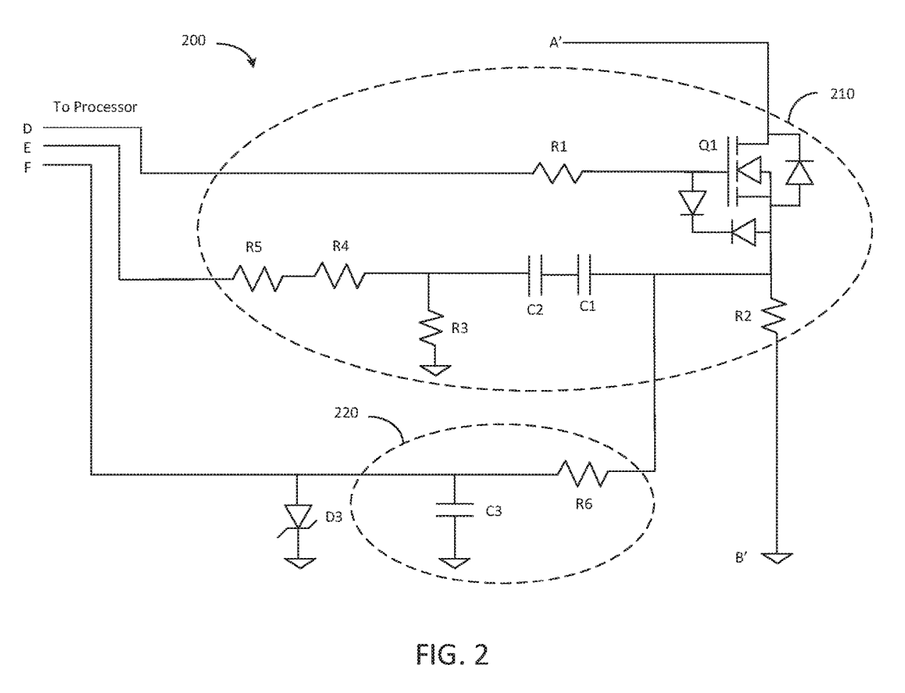
FIG. 2 is a topology of a reader circuit that can be used in the host device of FIG. 1, in accordance with an exemplary embodiment.

Referring to FIG. 2, a topology of a reader circuit 200 is shown, in accordance with an exemplary embodiment. The reader circuit 200 can be used as the reader circuit 134 in the host device 130 of FIG. 1. As shown in FIG. 2, in some embodiments, the reader circuit 200 comprises an AC excitation circuit 210 and a filter 220. The reader circuit 200 can be connected to a medical sensor device (e.g., sensor device 110 of FIG. 1) via connection points (e.g., power terminals) A' and B'.

The AC excitation circuit 210 is configured to generate an AC excitation voltage supplied at the power terminals A' and B'. In some embodiments, the AC excitation circuit 210 comprises a transistor Q1, where the source and drain of Q1 are connected to terminals A' and B', respectively. The gate of Q1 is connected to the processor of the host device (e.g., processor 136). In some embodiments, the drain of Q1 is grounded via a resistor R2, and the gate of Q1 is connected to the processor via a resistor R1 at a connection point D. The processor controls the ON/OFF state of Q1 by controlling the voltage level on the gate of Q1. A point E is configured to provide a square wave signal (e.g., 0-1.8 square wave signal), which is reduced by the resistors divider R3, R4, and R5 (to for example, 0.5V). With Q1 being turned on or off and the square wave signal being provided, a DC power provided by the internal battery of the host device (e.g., battery 132) is converted to an AC excitation signal. In some embodiments, capacitors C1 and C2 are used to remove the DC component from the AC excitation signal. The AC excitation signal is also called an "AC pilot signal." The AC pilot signal is on points A' and B', which is provided to the sensor device 110 through the interface 120. In further embodiments, the processor 136 can use the monitored AC pilot signal as a feedback to adjust the control of the gate of Q1. In some embodiments, the AC excitation signal has a low frequency of, for example, about 100 KHz. The amplitude of the AC excitation signal is as low as, for example, 0.5 V. It should be understood that the AC excitation circuit 210 is shown for illustration not for limitation. Any suitable circuit that can convert the DC power to the AC power may be used.

The AC pilot signal can excite a non-linear circuit at the sensor device side (e.g., non-linear circuit 112) to generate a response signal. The response signal can be received via the connection points A' and B' by the host device 130. In some embodiments, the low-pass filter 220 can filter the response signal for the processor 136 to further process. In some embodiments, the filter 220 comprises a low-pass RC filter, which includes one or more resistors R6 and one or more capacitors C3. The cut-off frequency of the filter 220 can be, for example, about 100 Hz to 1 KHz. The filtered response signal is provided to the processor 136 at a connection point F. In some embodiments, a diode D3 is used as electrostatic discharge (ESD) protection for analog to digital converter. It should be understood that the filter 220 is shown for illustration not for limitation. Any suitable low-pass filter can be used.

As discussed above, the magnitude (e.g., voltage level, current magnitude) of the response signal generated by the non-linear circuit 122 is higher than the magnitude of a response signal generated by a linear circuit, such as human skin or saline solution, which are essentially linear elements. Thus, the processor 136 compares the magnitude of the response signal with a threshold magnitude. If the response signal level is higher than the threshold level, the processor 136 determines that a sensor device is being attached. If the response signal level is not higher than the threshold level, the processor 136 determines that no sensor device is being attached. In some embodiments, the threshold level is a predefined value stored in the host device 130. In some embodiments, the magnitude of the response signal is an average magnitude over a period of time. In some embodiments, the magnitude of the response signal is a magnitude at a point of time (e.g., peak magnitude).

Figure 3A:
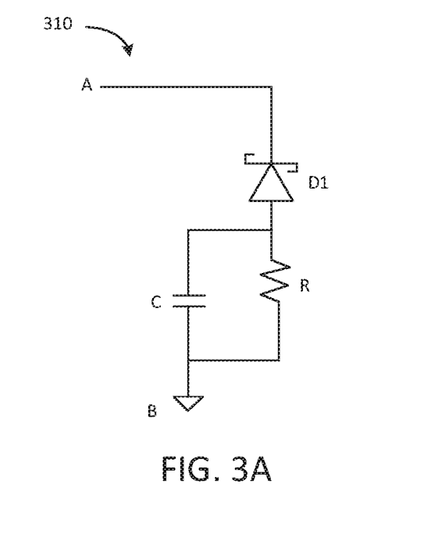
FIG. 3A is a topology of a non-linear circuit that can be used in the sensor device of FIG. 1, in accordance with an exemplary embodiment.
Figure 3B:
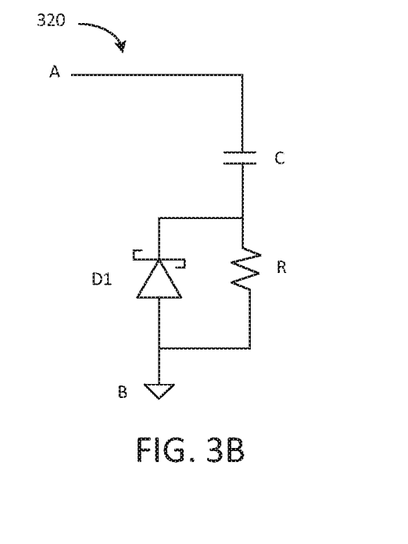
FIG. 3B is a topology of a non-linear circuit that can be used in the sensor device of FIG. 1, in accordance with another exemplary embodiment.

Referring to FIGS. 3A and 3B, topology of a first exemplary non-linear circuit 310 and topology of a second exemplary non-linear circuit 320 are shown. The non-linear circuits 310 and 320 can each be used as the non-linear circuit 112 of the sensor device 110 of FIG. 1. As shown in FIGS. 3A and 3B, in some embodiments, the non-linear circuit 310 and 320 each comprise a non-linear component—diode D1. The non-linear circuit 310 or 320 can be connected to a host device (e.g., host device 130 of FIG. 1) via connection points A and B. In circuit 310, diode D1 is connected in series with a resistor R between connection points A and B, and a capacitor C is connected in parallel with the resistor R. In circuit 320, the capacitor C is connected in series with the resistor R between connection points A and B, and diode D1 is connected in parallel with the resistor R. In an exemplary embodiment, the capacitor C has a capacitance of about 5 nF, the pull-down resistor R has a resistance of about 50 KΩ, and the AC excitation signal provided through connection points is 0.5 V with a frequency of 100 kHz. In some embodiments, the non-linear circuit 310 or 320 has a relatively low cut-off frequency in a range of, for example, 100 Hz-1 KHz, to avoid DC leakage in operation.

The non-linear circuit 310 or 320 can generate a DC response signal, which can be transferred via connection points A and B to the host device 130. Due to the nonlinear element D1, the magnitude of the response signal generated by the non-linear circuit 310 or 320 is higher than the magnitude of a response signal generated by a linear circuit, such as human skin or saline solution, which are essentially linear elements. It should be understood that non-linear circuits 310 and 320 are shown for illustration not for limitation. Any suitable non-linear circuit capable of generating greater response signal than linear elements can be used.

Figure 4A:
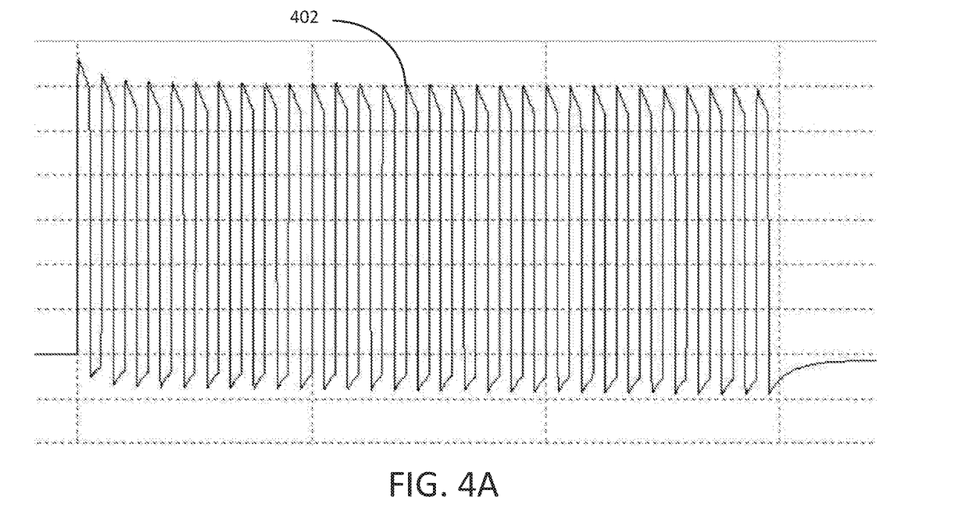
FIG. 4A is a graph of an AC pilot signal with a sensor device being attached, in accordance with an exemplary embodiment.
Figure 4B:
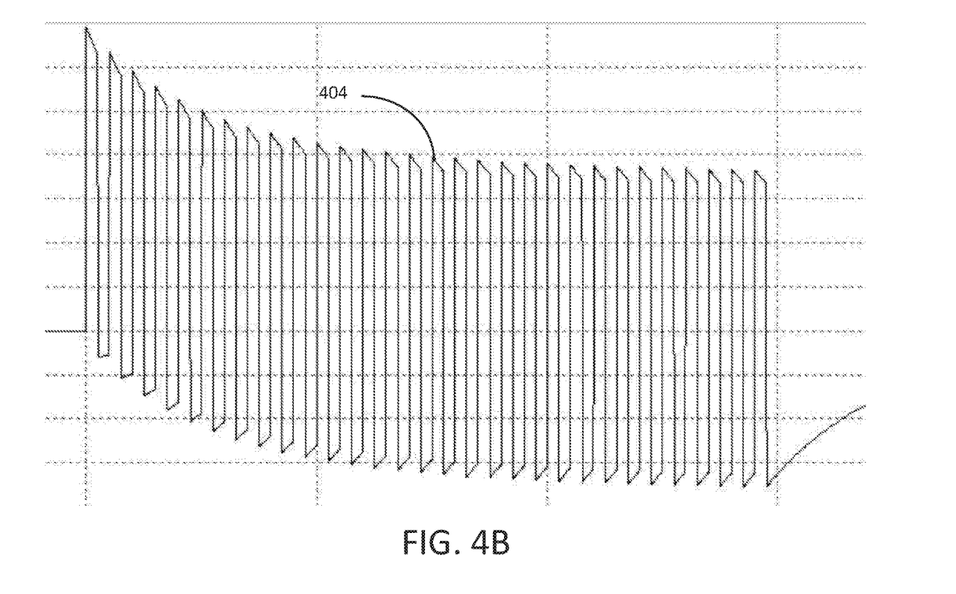
FIG. 4B is a graph of an AC pilot signal with no sensor device being attached, in accordance with an exemplary embodiment.
Figure 5A:
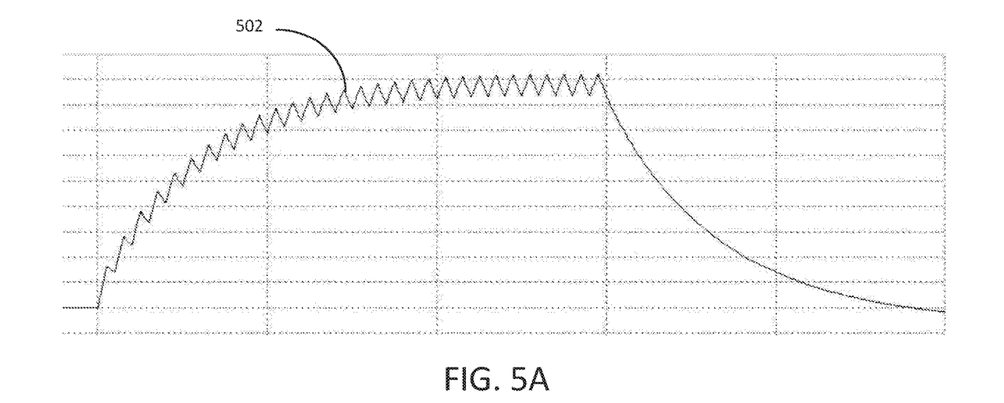
FIG. 5A is a graph of a response signal with a sensor device being attached, in accordance with an exemplary embodiment.
Figure 5B:
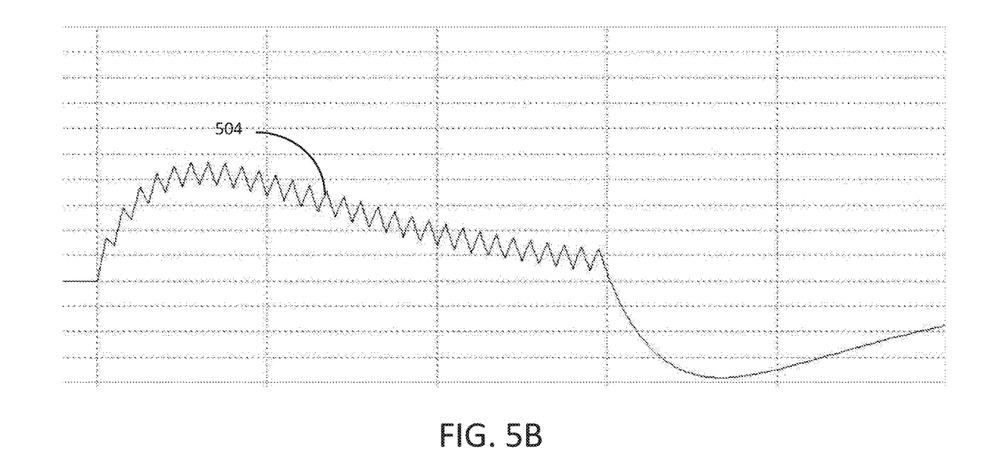
FIG. 5B is a graph of a response signal with no sensor device being attached, in accordance with an exemplary embodiment.
Figure 6A:
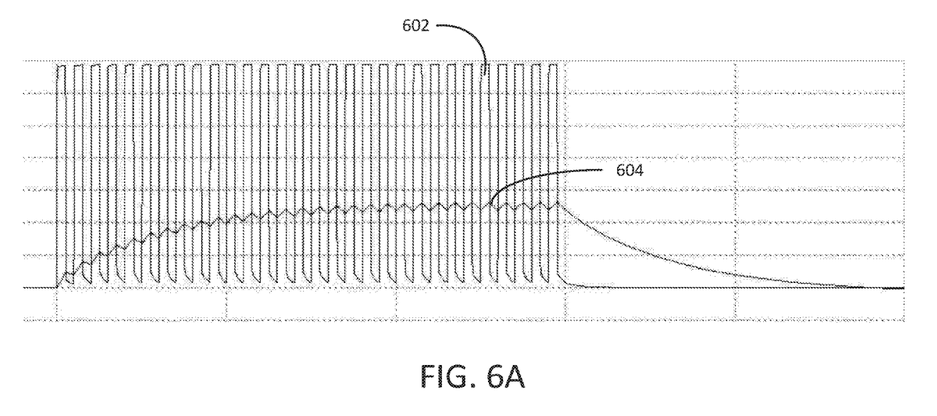
FIG. 6A shows a graph of the AC pilot signal and response signal with a sensor device being attached, in accordance with an exemplary embodiment.
Figure 6B:
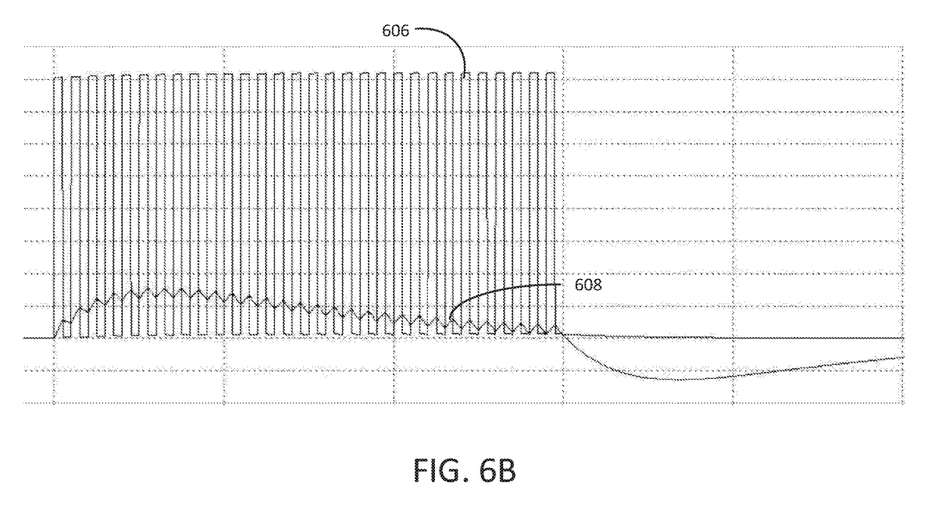
FIG. 6B is a graph of the AC pilot signal and response signal with no sensor device being attached, in accordance with an exemplary embodiment.

FIGS. 4A through 6D show simulated results for a situation where a sensor device is being attached to a host device and another situation where no sensor device is being attached to a host device. For the situation where no sensor device is being attached, some linear element such as human skin may be attached to the connector of the host device. Curve 402 in FIG. 4A shows an AC pilot signal with a sensor device being attached, while curve 404 in FIG. 4B shows an AC pilot signal with no sensor device being attached. The AC pilot signal can be monitored at, for example, connection points A and B of FIG. 2. Curve 502 in FIG. 5A shows a response signal with a sensor device being attached, while curve 504 in FIG. 5B shows a response signal with no sensor device being attached. The response signal can be monitored at, for example, connection point F of FIG. 2. FIG. 6A shows AC pilot signal 602 and corresponding response signal 604 where a sensor device is being attached. FIG. 6B shows AC pilot signal 606 and corresponding response signal 608 where no sensor device is being attached. It can be seen that the response signal generated by a sensor device reaches a considerably higher level than the response signal generated otherwise under similar configuration of the AC pilot signal. Therefore, contact of a sensor device can be distinguished from contact otherwise (e.g., human skin).

Figure 7:
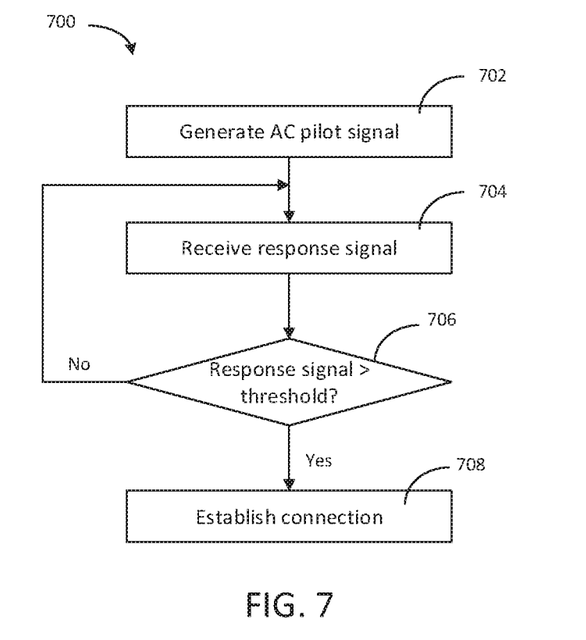
FIG. 7 is a flow chart of a method for detecting a medical sensor device being attached to a host device, in accordance with an exemplary embodiment.

Referring to FIG. 7, a flow chart 700 of a method for detecting the attachment of a medical sensor device to a host device is shown in accordance with an exemplary embodiment. The method can be executed by a host device (e.g., host device 130 of FIG. 1). At an operation 702, the host device generates an AC pilot signal. The AC pilot signal is provided at connection points A' and B' of the connector 124 at the side of the host device 130. If the sensor device 110 is being attached to the host device 130 through the interface 120, the AC pilot signal is supplied to the sensor device 110 via the connection points A-A' and B-B'.

At an operation 704, the host device 130 receives a response signal at the connection points A' and B'. If the sensor device 110 is being attached to the host device 130, the response signal reflects the response of the non-linear circuit 112 in the sensor device 110. If no sensor device is being attached, the response signal may reflect the response otherwise (e.g., human skin).

At an operation 706, the host device 130 determines whether the magnitude (e.g., voltage level, current magnitude) of the response signal is greater than a predefined threshold magnitude. In some embodiments, the magnitude of the response signal is an average magnitude over a period of time. In some embodiments, the magnitude of the response signal is a magnitude at a point of time (e.g., peak magnitude).

In response to determining that the magnitude of the response signal is not greater than the threshold magnitude (i.e., "No" in operation 706), the method proceeds to the operation 704 because it is indicated that no sensor device is being attached to the host device. In response to determining that the magnitude of the response signal is greater than the threshold magnitude (i.e., "Yes" in operation 706), the method proceeds to an operation 708, where the host device 130 establishes a connection with the sensor device 110. In particular, the host device 130 turns on power to supply to the sensor device 110 and communicates data with the sensor device 110.

In some embodiments, in order to mitigate the risk of misuse or other rare events resulting in a high DC offset without the sensor device 110 being attached, the host device 130 can initiate a secondary handshake process before establishing the connection at the operation 708. In particular, the sensor device 130 can send a request for acknowledgement to the sensor device 110 via the interface 120. In response to the request, the sensor device 110 sends an acknowledgement message to the host device 130. In response to receiving the acknowledgement message, the host device 130 determines that the sensor device 130 is present and establishes the connection with it.

In addition to any previously indicated modification, numerous other variations and alternative arrangements may be devised by those skilled in the art without departing from the spirit and scope of this description, and appended claims are intended to cover such modifications and arrangements. Thus, while the information has been described above with particularity and detail in connection with what is presently deemed to be the most practical and preferred aspects, it will be apparent to those of ordinary skill in the art that numerous modifications, including, but not limited to, form, function, manner of operation and use may be made without departing from the principles and concepts set forth herein. Also, as used herein, the examples and embodiments, in all respects, are meant to be illustrative only and should not be construed to be limiting in any manner.

What is claimed is:

1. A host device for medical sensor devices, the host device comprising:
   a connector comprising a first connection point and a second connection point configured to connect to a medical sensor device;
   a reader circuit comprising:
      an excitation circuit configured to generate an alternating current (AC) pilot signal supplied at the first connection point and the second connection point; and
      a filter; and
   a processor configured to:
      control the excitation circuit to generate the AC pilot signal;
      receive a response signal from the first connection point and the second connection point, wherein the response signal is filtered by the filter;
      compare a magnitude of the response signal with a threshold magnitude; and
      in response to determining the magnitude of the response signal is greater than the threshold magnitude, establish a connection with the medical sensor device being attached to the host device.

2. The host device of claim 1, wherein the excitation circuit comprises a transistor, a source and a drain of the transistor are connected to the first terminal and the second terminal respectively, and the processor controls a gate of the transistor to turn on or off the transistor.

3. The host device of claim 1, wherein the filter is a low-pass filter with a cut-off frequency in a range of about 100 Hz to 1 KHz.

4. The host device of claim 1, wherein the filter is a RC filter that comprises one or more resistors and one or more capacitors.

5. The host device of claim 1, wherein the AC pilot signal has a frequency of about 100 KHz and an amplitude of about 0.5 V.

6. The host device of claim 1, wherein the connector is capable of being connected to various types of medical sensor devices.

7. The host device of claim 1, wherein the connector further comprises a third connection point for communicating data with the medical sensor device.

8. The host device of claim 1, wherein the host device further comprises a battery, establishing a connection with the medical sensor device comprises:
   supplying power from the battery to the medical sensor device; and
   communicating physiological data with the medical sensor device.

9. The host device of claim 8, wherein establishing a connection with the medical sensor device further comprises performing a handshake process with the medical sensor device.

10. The medical sensor device of claim 9, wherein the non-linear circuit comprises a diode and a resistor connected in series between the first connection point and the second connection point, and a capacitor connected in parallel with the resistor.

11. The medical sensor device of claim 9, wherein the connector further comprises a third connection point for communicating data with the host device.

12. A medical sensor device comprising:
   a sensor for monitoring physiological conditions of a patient or a fetus;
   a connector comprising a first connection point and a second connection point configured to connect to a host device; and
   a non-linear circuit disposed between the first connection point and a second connection point, wherein the non-linear circuit is configured to generate a direct current (DC) response signal in response to an AC pilot signal received from the host device via the connector, wherein the DC response signal is filtered by a filter and transmitted to a processor of the host device.

13. The medical sensor device of claim 12, wherein the sensor comprises at least one of ECG electrodes, EEG electrodes, blood pressure sensor, temperature sensor, and pulse oximeter.

14. A method for detecting a medical sensor device being attached to a host device, wherein the host device comprises a first connection point and a second connection point configured to connect to the medical sensor device, the method comprising:
   generating an AC pilot signal supplied at the first connection point and the second connection point;
   receiving a response signal from the first connection point and the second connection point;
   low-pass filtering the response signal;
   comparing a magnitude of the response signal with a threshold magnitude; and
   in response to determining the magnitude of the response signal is greater than the threshold magnitude, establishing a connection with the medical sensor device being attached to the host device.

15. The method of claim 14, wherein the medical sensor device comprises at least one of an ECG monitor, EEG monitor, NIBP monitor, peripheral oxygen saturation (SpO2) monitor, and temperature monitor.

16. The method of claim 14, wherein the AC pilot signal has a frequency of about 100 KHz and an amplitude of about 0.5 V.

17. The method of claim 14, wherein establishing a connection with the medical sensor comprises:
   supplying power from the host device to the medical sensor; and
   communicating physiological data with the medical sensor.

18. The method of claim 17, wherein establishing a connection with the medical sensor further comprises performing a handshake process with the medical sensor.

* * * * *